Figure 1:
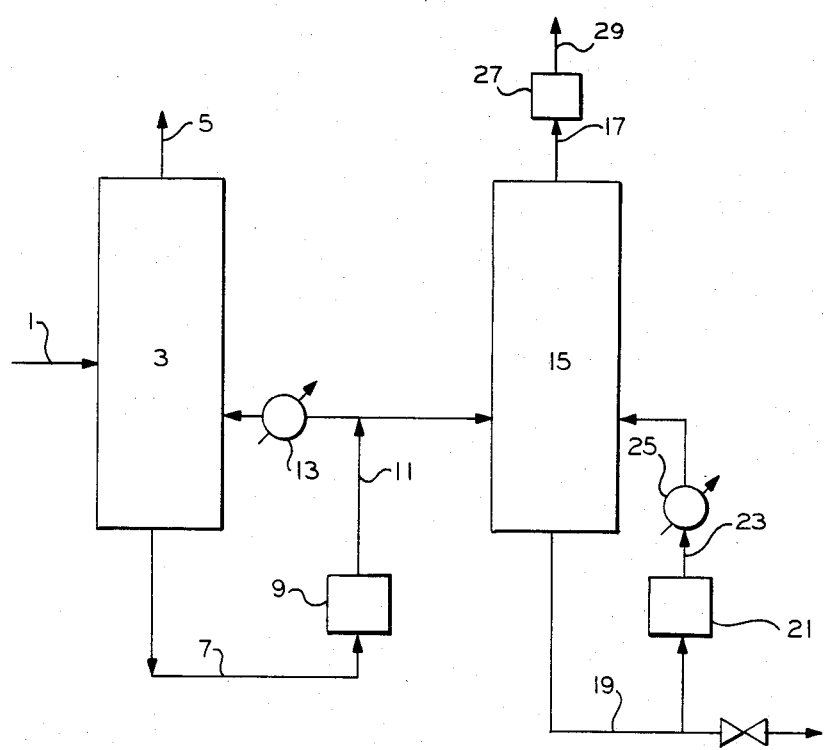

United States Patent [19]

Cleary

[11] Patent Number: 4,501,902

[45] Date of Patent: Feb. 26, 1985

[54] N-METHYL PYRROLIDONE-2 PURIFICATION

[75] Inventor: James W. Cleary, Bartlesville, Okla.

[73] Assignee: Phillips Petroleum Company, Bartlesville, Okla.

[21] Appl. No.: 451,668

[22] Filed: Dec. 21, 1982

[51] Int. Cl.³ .......................................... C07D 206/267
[52] U.S. Cl. .................................. 548/555; 528/388; 564/216; 549/87; 568/27
[58] Field of Search ........................................... 548/555

[56] References Cited

U.S. PATENT DOCUMENTS

| | | | |
|---|---|---|---|
| 2,828,307 | 3/1958 | Soeterbroek et al. | 548/555 |
| 2,939,869 | 6/1980 | Carlson | 548/555 |
| 2,964,535 | 12/1960 | Clements | 548/555 |
| 3,658,659 | 4/1972 | Cottle | 203/76 |
| 3,707,528 | 12/1972 | Miles | 260/79 |
| 3,783,138 | 1/1974 | Miles et al. | 260/79 |
| 4,014,900 | 3/1977 | Pusztaszeri | 548/555 |

FOREIGN PATENT DOCUMENTS 2324921 8/1973 German Democratic Rep. .................................. 548/555

Primary Examiner—Glennon H. Hollrah
Assistant Examiner—D. B. Springer
Attorney, Agent, or Firm—A. W. Umphlett

[57] ABSTRACT

A process for removing compounds from aprotic solvents in which aprotic solvent containing at least one acidic compound is contacted with a solid inorganic compound chosen from alkaline earth carbonates, alkaline earth hydroxides, alkaline earth oxides, and alumina in which the contact of the solvent with a solid inorganic compound is by the process of fluidized bed contact, stirred slurry contact or trickle bed contact. Contaminated NMP from poly(phenylene sulfide) production is substantially freed of acidic contaminants by a series of fractionations with a treatment of the kettle liquid of at least one fractionation by the method described above and/or a treatment of the overhead of the last fractionation in series by the method described above.

11 Claims, 1 Drawing Figure

N-METHYL PYRROLIDONE-2 PURIFICATION

BACKGROUND OF THE INVENTION

This invention relates to the treatment of aprotic solvents. In one of its aspects this invention relates to the removal of acidic compounds from aprotic solvents. In still another of its aspects this invention relates particularly to the treatment of N-methyl-2-pyrrolidone for the removal of phenol and other acidic compounds.

In processes for the recovery of N-methyl-2-pyrrolidone (NMP) which is used in the production of poly(phenylene sulfide) the recovery is usually effected by employing fractionation columns in series. Into the first column is fed a combination of materials which results from the poly(phenylene sulfide) production process which has N-methyl-2-pyrrolidone as the major constituent with water, dichlorobenzene, light materials, and various acidic materials such as phenol, N-methylsuccinimide, dimethylpyrrolidone as impurities. The first fractionation column is operated at conditions to remove the water, dichlorobenzene, and other materials lighter than the NMP. Acidic contaminants are not completely removed in the operation of this fractionator.

It is desirable, however, to keep acidic impurities in NMP that is used for poly(phenylene sulfide) production to a minimum since their presence, particularly phenol and N-methylsuccinimide, can upset the stoichiometry of the reaction and result in the formation of polymer that is off-specification. Under usual operating conditions further fractionation of the kettle product from the first fractionation column will produce NMP overhead which still contains acidic impurities at a level above the minimum desired. By the process of this invention a method is provided by which kettle liquid and/or overhead product from the fractionation columns can be treated for the removal of acidic contaminants thereby reducing the amount of material that must be discarded or retreated.

N-methyl-2-pyrrolidone is typical of aprotic solvents and the purification of this material is also typical of the purification processes for other aprotic solvents. The invention exemplified herein is applicable to the removal of acidic contaminants from aprotic solvents in general.

It is therefore an object of this invention to provide a method for removing acidic contaminants from aprotic solvents. It is still another object of this invention to provide a method for removing acidic contaminants associated with N-methyl-2-pyrrolidone recovered from use in the production of poly(phenylene sulfide). It is still another object of this invention to facilitate the recovery of N-methyl-2-pyrrolidone from a poly(phenylene sulfide) production that can be recycled for further production of poly(phenylene sulfide).

Other aspects, objects and advantages of this invention will become apparent upon study of this specification, the drawings and the appended claims.

STATEMENT OF THE INVENTION

According to the process of this invention, a method is provided for removing acidic compounds from aprotic solvents in which an aprotic solvent containing at least one acidic compound is contacted with an amount of an inorganic compound chosen from among alkaline earth carbonates, alkaline earth hydroxides, alkaline earth oxides, and alumina that is sufficient to reduce the acidic compound content of the solvent.

In preferred embodiments of the invention the contact of the aprotic solvent with the inorganic compound is conducted by a process of fluidized bed contact, stirred slurry contact, or trickle bed contact.

In specific embodiments of the invention a process is provided for recovery of N-methyl-2-pyrrolidone (NMP) from poly(phenylene sulfide) production in which fractionation columns are employed in series to remove water, dichlorobenzene and low boiling contaminants from NMP in which in a first fractionator NMP contaminated with water, dichlorobenzene, low boiling contaminants and acidic compounds is fractionated to remove overhead the water, dichlorobenzene and low boiling compounds. The kettle liquid from this first fractionator is further fractionated in a second fractionator to remove overhead a product consisting essentially of NMP. The kettle liquid of either or both of the fractionation columns and/or the overhead from the second fractionator is treated by contact with an inorganic compound as described above thereby at least reducing or substantially removing acidic contaminants from the NMP.

The process of this invention is best illustrated in conjunction with the drawing which is a line representation of a process for treating NMP recovered from poly(phenylene sulfide) production for removal of contaminants.

Referring now to the drawing, the feedstock containing NMP contaminated with water, dichlorobenzene (DCB), low boiling materials, and acid contaminates such as phenol and N-methylsuccinimide is fed through line 1 into fractionator 3. The fractionator is maintained at operating conditions such that water, dichlorobenzene, and low boiling materials are removed overhead through line 5 and a kettle liquid of NMP and higher boiling materials contaminated with acid contaminants is removed through line 7.

By the process of this invention, the material removed through line 7 is passed in contact with an inorganic compound as designated above, such as alumina in a ratio of NMP to inorganic compound in a range of about 0.1/1 to 1000/1, preferably about 1/1 to about 100/1. The means of contact in contacting zone 9 can be chosen from such processes as fluidized bed contact of the contaminated liquid solvent with solid inorganic compound, stirred contact of a slurry of the solid inorganic compound with a contaminated solvent, or trickle bed contact of the contaminated solvent passing through a bed of solid inorganic compound. The contact can be made at room temperature or at an elevated temperature up to the operation temperature of the fractionating column. Provision is, of course, made for removal of inorganic compound that has become essentially saturated with the acid contaminant so that further contact with the solvent would be ineffective. This can be accomplished by having dual contactors for alternate use or means for withdrawing inorganic compound with replacement by fresh material on a continuous basis.

Treated NMP effluent from contactor 9 is passed through line 11 either back to the first fractionator 3, optionally through a heat exchanger 13, or passed into a second fractionator 15 which is maintained at conditions to remove overhead through line 17 a stream that is essentially NMP, while higher boiling materials are removed through kettle liquid line 19. Here again, the kettle liquid can be circulated via line 19 through a contact system 21 like that described as contactor 9 and passed through line 23, optionally through heat exchanger 25 into the second fractionator 15.

The use of either contactor 9, contactor 21 or the two contactors in combination provides a reduction in the amount of acidic contaminant in the NMP removed through line 17. It is also within the scope of the present invention to provide a contactor 27 on the overhead line from the second fractionator thereby removing residual acid contaminant before passing NMP through line 29 for recycling or other use.

EXAMPLE I

A plug of glass wool was placed in a gas drying tube about 0.5 inch inner diameter and the specified absorbent was added to give a bed about 1.5 inches in height. The contaminated NMP, about 80 mL, was allowed to drain once through the tube at about 25° C. except for the alumina absorbent which was in the form of much coarser particles than the others. The flow through the bed in that run was so rapid that the NMP was passed through the tube 5 times. On a one time through basis, the volume NMP per volume absorbent was about 17 to 1.

The contaminated NMP was obtained from a commercial plant run in which an upset had occurred during the polymerization of poly(phenylene)sulfide. The NMP recovered from a purification column such as stream 17 from column 15 of FIG. 1 operated without benefit of any of the contactors 9, 21, or 27, was found to be contaminated with various undesirable components such as phenol, N-methylsuccinimide, N-methylacetamide and/or 1,3-dimethylpyrrolidone, diphenyl ether and an unknown compound of molecular weight 127.

Analyses of the NMP in this Example and the others were made with a Perkin Elmer Sigma 3 gas chromatograph with a 10 foot, ⅛ inch nickel column containing 6 percent K20M, a commercial absorbent, on 35/60 mesh Chromasorb T.

The absorbents employed and the results obtained are set forth in Table 1.

TABLE 1
TREATMENT OF CONTAMINATED NMP BY TRICKLE BEDS AT 25° C.

| | Run | | | | |
|---|---|---|---|---|---|
| | 1 | 2 | 3 | 4 | 5 |
| Adsorbent | None | Ca(OH)$_2$ | CaCO$_3$ | MgO | Al$_2$O$_3$ |
| Analysis of NMP, Wt % | | | | | |
| NMP | 98.63 | 99.34 | 99.45 | 99.13 | 99.42 |
| Other[a] | 1.37 | 0.66 | 0.55 | 0.87 | 0.58 |
| Minor Constituents | | | | | |
| Lights | 0 | 0.01 | 0 | 0 | 0.05 |
| Methylthiobenzene | Tr[c] | Tr | 0.01 | 0 | Tr |
| N—Methylacetamide and/or 1,3-Dimethylpyrrolidone[b] | 0.27 | 0.14 | 0.13 | 0.20 | 0.14 |
| MW-127[d] | 0.23 | 0.15 | 0.07 | 0.04 | 0.04 |
| N—Methylsuccinimide | 0.39 | 0.18 | 0.13 | 0.30 | 0.12 |
| Phenol | 0.29 | 0.11 | 0.13 | 0.24 | 0.14 |
| Diphenyl ether | 0.20 | 0.03 | 0.03 | 0.05 | 0.03 |
| "Others" | Tr | 0.05 | Tr | 0.05 | 0.05 |
| Heavies | 0 | Tr | 0.04 | Tr | 0 |

[a]No DCB was present in any of these samples.
[b]These peaks almost coincide.
[c]Trace
[d]Unidentified compound having a molecular weight of about 127

The results shown in Table 1 illustrate that the treatments reduced the amounts of minor components associated with the contaminated NMP from 1.37 weight percent to a range of 0.55 to 0.87 weight percent. Calcium carbonate was the most effective absorbent and magnesium oxide was the least effective absorbent in this test. Generally, about ½ or more of the phenol, N-methylsuccinimide, N-methylacetamide and/or 1,3-dimethylpyrrolidone and unknown compound of molecular weight 127 were removed by the Ca(OH)$_2$, CaCO$_3$ and Al$_2$O$_3$. However, the Ca(OH)$_2$ only removed about 35 percent of the unknown compound in this test.

EXAMPLE II

In the stirred slurry runs, 4 g of the specified absorbent was added to a glass flask containing about 100 g of a sample of the contaminated NMP employed as source material in Example I and a magnetic stirring bar. The weight ratio of NMP to absorbent was 25 to 1 in each run. When a temperature of 180° C. was to be used, the NMP was heated just above 180° C. before adding the absorbent. In each run, the slurry was stirred for 30 minutes and the reaction mixture was filtered through a sintered glass filter. Each filtrate was subsequently analyzed as before.

The absorbents employed and the results obtained are given in Table 2.

TABLE 2
TREATMENT OF CONTAMINATED NMP BY STIRRED SLURRIES AT 25° C. AND/OR 180° C.

| | Run | | | | | | |
|---|---|---|---|---|---|---|---|
| | 1 | 2 | 3 | 4 | 5 | 6 | 7 |
| Adsorbent | None | CaO | CaO | Ca(OH)$_2$ | CaCO$_3$ | MgO | Al$_2$O$_3$ |
| Temperature, °C. | 25 | 25 | 180 | 180 | 180 | 180 | 180 |
| Analysis of NMP, Wt. % | | | | | | | |
| NMP | 98.63 | 99.44 | 99.59 | 99.44 | 99.33 | 99.40 | 99.36 |

TABLE 2-continued
TREATMENT OF CONTAMINATED NMP BY STIRRED SLURRIES AT 25° C. AND/OR 180° C.

| | Run | | | | | | |
|---|---|---|---|---|---|---|---|
| | 1 | 2 | 3 | 4 | 5 | 6 | 7 |
| Other[a] | 1.37 | 0.56 | 0.41 | 0.56 | 0.67 | 0.60 | 0.64 |
| Minor Constituents | | | | | | | |
| Lights | 0 | 0 | 0 | Tr[e] | 0 | Tr | 0 |
| Methylthiobenzene | Tr | 0.01 | 0 | Tr | Tr | Tr | Tr |
| N—Methylacetamide and/or 1,3-Dimethylpyrrolidone[b] | 0.27 | 0.14 | 0.08 | 0.09 | 0.15 | 0.12 | 0.14 |
| MW-127[d] | 0.23 | 0.06 | 0.04 | 0.05 | 0.07 | 0.06 | 0.12 |
| N—Methylsuccinimide | 0.39 | 0.14 | 0.11 | 0.16 | 0.21 | 0.19 | 0.17 |
| Phenol | 0.29 | 0.13 | 0.09 | 0.14 | 0.14 | 0.12 | 0.14 |
| Diphenyl ether | 0.20 | 0.03 | 0.03 | 0.06 | 0.06 | 0.06 | 0.06 |
| "Others" | Tr | 0.06 | 0.07 | 0.05 | 0.04 | 0.05 | 0.02 |
| Heavies | 0 | 0 | 0 | 0 | 0 | 0 | 0 |

[a]No DCB was present in any of these samples.
[b]These peaks almost coincide.
[c]Trace
[d]Unidentified compound having a molecular weight of about 127

The results obtained in Table 2 show that a stirred slurry of CaO at room temperature, 25° C., was found to be as effective as a trickle bed of CaCO3 at 25° C. (Run 3, Table 1) in removing minor components found in contaminated NMP. The efficiency of CaO was improved at 180° C. compared to 25° C. At 25° C., the CaO removed about 59 weight percent of the minor components and at 180° C. it removed about 70 weight percent of the minor components. In the tests, CaO at 180° C. was shown to be more effective than Ca(OH)2, CaCO3, MgO and Al2O3 at 180° C. in removing the minor components of the contaminated NMP. NMP, treated with CaO, contained only 0.41 weight percent of such components compared to 0.56 to 0.67 weight percent found in NMP treated with the other absorbents.

In comparing the results at 180° C. with the various absorbents, the CaO was found to remove about 69 weight percent of the phenol relative to values ranging from about 52 to 59 weight percent for the others. The CaO was found to remove about 72 weight percent of N-methylsuccinimide relative to values ranging from about 41 to 59 weight percent for the others. The CaO was found to remove about 85 weight percent of diphenyl ether relative to about 70 weight percent for the others. The CaO was found to remove about 83 weight percent of unknown compound of molecular weight 127 relative to values ranging from about 48 to 78 weight percent for the others. And finally, the CaO was found to remove about 70 weight percent of N-methylacetamide and/or 1,3-dimethylpyrrolidone relative to values ranging from about 44 to 67 weight percent for the others.

Under the test conditions employed, CaO is the preferred absorbent. The others performed less effectively but still acceptably.

The results obtained in Examples I and II, particularly in Example II at 180° C. indicate that a contacting bed can also be employed subsequent to an NMP recovery column to substantially reduce minor components that are not effectively removed from the NMP in such a column. Such a bed represents another embodiment of this invention.

The results obtained in trickle beds or stirred slurries with contaminated NMP indicate that, in addition to NMP, other aprotic solvents such as sulfolane, dimethylsulfoxide, dimethylformamide and dimethylacetamide that are similarly contaminated with acidic materials can be purified in like fashion. Such beds can be used in conjunction with one or more recovery columns such as in this invention.

EXAMPLE III

A sample of crude NMP obtained as kettle liquid from a commercially operated fractionator such as fractionator 3, FIG. 1, was divided into 5 portions of 100 mL each. Each portion was magnetically stirred for 30 minutes at 180° C. with 5 g of the specified inorganic compound absorbent, when used. The weight ratio of crude NMP to absorbent was about 25 to 1 in each instance. The cooled liquids were then individually analyzed as before, to determine their compositions. The results are tabulated in Table 3.

TABLE 3
TREATMENT OF CRUDE NMP WITH INORGANIC ABSORBENTS

| | Run | | | | |
|---|---|---|---|---|---|
| | 1 | 2 | 3 | 4 | 5 |
| Absorbent | None | CaO | Ca(OH)2 | CaCO3 | Al2O3 |
| Analysis of NMP, Wt % | | | | | |
| NMP | 96.86 | 98.97 | 98.60 | 97.94 | 98.06 |
| Other[a] | 3.14 | 1.03 | 1.40 | 2.06 | 1.94 |
| Minor constituents | | | | | |
| Lights | 0.01 | 0.01 | 0.01 | Tr[c] | Tr |
| Methylthiobenzene | 0.05 | 0.04 | 0.04 | 0.04 | 0.04 |
| N—Methylacetamide and/or 1,3-Dimethylpyrrolidone[b] | 0.31 | 0.30 | 0.28 | 0.31 | 0.30 |
| MW-127[d] | 0.12 | 0.06 | 0.09 | 0.12 | 0.12 |
| N—Methylsuccimide | 0.98 | 0.30 | 0.58 | 1.10 | 1.05 |
| Phenol | 0.62 | 0.07 | 0.10 | 0.16 | 0.14 |
| Diphenyl ether | 0.50 | 0.14 | 0.14 | 0.16 | 0.15 |

TABLE 3-continued
TREATMENT OF CRUDE NMP WITH INORGANIC ABSORBENTS

| | Run | | | | |
|---|---|---|---|---|---|
| | 1 | 2 | 3 | 4 | 5 |
| "Others" | 0.38 | 0.02 | 0.03 | 0.03 | 0.03 |
| Heavies | 0.17 | 0.09 | 0.13 | 0.13 | 0.10 |

[a]No DCB was present in any of these samples.
[b]These peaks almost coincide.
[c]Trace
[d]Unidentified compound having a molecular weight of about 127

The results in Table 3 show that each absorbent employed was effective in reducing the impurities in the crude NMP from the initial 3.14 weight percent to a lesser value which ranged from 1.03 to 2.06 weight percent. In terms of decrease of impurities following treatment, the corresponding values show a decrease ranging from 67 to 34 percent.

It is desirable to remove the impurities, especially phenol, from the crude NMP to increase the recovery of purified NMP from the second fractionator 15. It is known that phenol will codistill with NMP when its concentration approaches 20 weight percent of the NMP.

The results further show that calcium oxide was the most effective absorbent tested. It removed about 89 percent of the phenol, about 70 percent of the N-methylsuccinimide and diphenyl ether. On the other hand, it was almost ineffective in reducing the concentration of N-methylacetamide and 1,3-dimethylpyrrolidone. Removal of all of the latter components and the remainder listed in Table 3 is not considered of paramount importance, however.

Calcium hydroxide was less effective than calcium oxide as an absorbent in this process in removing phenol (84% vs. 89%) and much less effective in removing N-methylsuccinimide (41% vs. 69%). Calcium carbonate and alumina were the least effective absorbents tested but still they removed about 74 to 77%, respectively, of the phenol.

The results further indicate that a contacting bed can be effectively employed such as contactor 9 in FIG. 1 to improve the efficiency of the recovery process.

EXAMPLE IV

A sample of kettle bottom liquid obtained from a NMP recovery column such as fractionator 15 was divided into 3 portions of 100 mL each. Each portion was stirred magnetically for 30 minutes at 180° C. with the specified amount (5 g or 10 g) of CaO, when employed. The weight ratio of kettle bottom liquid to CaO was about 21 to 1 in run 2 and about 22 to 1 in run 3. Each cooled liquid was then analyzed as before, to determine sample compositions. The results are presented in Table 4.

TABLE 4
TREATMENT OF KETTLE BOTTOMS FROM THE NMP RECOVERY COLUMN WITH CALCIUM OXIDE

| | Run | | |
|---|---|---|---|
| | 1 | 2 | 3 |
| Calcium oxide, g | 0 | 5 | 10 |
| Analysis of NMP, area % | | | |
| NMP | 66.24 | 81.32 | 81.87 |
| Other[a] | 33.76 | 18.68 | 18.13 |
| Minor Constituents | | | |
| Lights | 0 | 0.10 | 0.16 |
| Methylthiobenzene | 0.01 | 0.02 | 0.04 |
| N—Methylacetamide and/or | 0.14 | 0.10 | 0.12 |
| 1,3-Dimethylpyrrolidone[b] | | | |
| MW-127[c] | 0.46 | 0.21 | 0.19 |
| N—Methylsuccinimide | 0.51 | 0.13 | 0.11 |
| Phenol | 16.91 | 5.63 | 3.86 |
| Diphenyl ether | 1.94 | 2.32 | 2.38 |
| "Others" | 4.82 | 5.79 | 5.97 |
| Heavies | 8.29 | 4.34 | 4.97 |

[a]No DCB was present in these samples.
[b]These peaks almost coincide.
[c]Unidentified compound having a molecular weight of about 127

The results in Table 4 are given in area percent since the response factors of a significant amount of minor components, especially the unknowns, are not known. The treatments in runs 2, 3, each left about the same total amount of minor components, about 18 percent of the original content of about 34 percent. This corresponds to a reduction of about 45 percent of the original minor components by the treatment. However, significant amounts of phenol and N-methylsuccinimide were removed. In run 2, which employed 5 weight percent CaO as absorbent, the phenol content was decreased about 67 weight percent and the N-methylsuccinimide content was decreased about 75 weight percent. In run 3, which employed 10 weight percent CaO as absorbent, the phenol content was decreased about 77 weight percent and the N-methylsuccinimide content was decreased about 78 weight percent. The amounts of heavies and unknown molecular weight 127 were nearly halved by the treatments. The significance of the treatment upon kettle bottom product which must be suitably disposed of and increasing the recovery of NMP are illustrated as follows:

In a commercial operation the kettle bottoms of a NMP recovery column are drawn off at the rate of about 3 barrels per day in order to keep the concentration of phenol in the kettle at less than about 20 percent. Vacuum distillation of the kettle bottoms recovers only a portion of the NMP since the remainder is complexed with the phenol and is difficult to separate therefrom. The kettle bottoms are about ⅔ NMP which amounts to about 2 barrels per day NMP (110 gallons per day) which is normally lost. By practicing the invention, it becomes feasible to reduce the amount of kettle bottom product from about 3 barrels per day to about 1 barrel per day, thus substantially reducing the amount of kettle bottom product to be disposed of and materially increasing the amount of NMP that can be recovered since the treated kettle bottom product can be recycled to the NMP recovery column 15.

The results further indicate that a contacting bed such as contactor 21 of FIG. 1 can be advantageously employed in the recovery process to more efficiently recover NMP.

I claim:

1. A process for removing acidic compounds from N-methyl-2-pyrrolidone(NMP); in which NMP containing at least one acidic compound is contacted with an amount of an inorganic compound chosen from among the group consisting of alkaline earth carbonates, alkaline earth hydroxides, alkaline earth oxides and alumina said amount sufficient to reduce the acidic compound content of said solvent thereby producing NMP of reduced acid content and said NMP of reduced acid content is removed from contact with said inorganic compound.

2. A process for recovery of NMP from poly(phenylene sulfide) production in which fractionation columns are employed in series to remove water, dichlorobenzene and low boiling contaminants from NMP comprising:
    (a) fractionating in a first fractionator NMP contaminated with water, dichlorobenzene, low boiling contaminants and acidic compounds to remove overhead the water, dichlorobenzene and low boiling contaminants and produce a kettle liquid comprising NMP contaminated with acidic compounds;
    (b) treating the kettle liquid of said first fractionator by the process of claim 1 to remove acidic compounds; and
    (c) further fractionating the treated kettle liquid of said first fractionator in a second fractionator to remove overhead a product comprising NMP.

3. A process for recovery of NMP from poly(phenylene sulfide) production in which fractionation columns are employed in series to remove water, dichlorobenzene and low boiling contaminants from NMP comprising:
    (a) fractionating in a first fractionator NMP contaminated with water, dichlorobenzene, low boiling contaminants and acidic compounds to remove overhead the water, dichlorobenzene and low boiling compounds and produce a kettle liquid comprising NMP contaminated with acidic compounds, and
    (b) further fractionating the kettle liquid of said first fractionator in a second fractionator to remove overhead a product comprising NMP with treatment of the treated kettle liquid of said second fractionator by the method of claim 1 to remove acidic compounds with recycle of the kettle liquid to said second fractionator.

4. A process for recovery of NMP from poly(phenylene sulfide) production in which fractionation columns are employed in series to remove water, dichlorobenzene and low boiling contaminants from NMP comprising:
    (a) fractionating in a first fractionator NMP contaminated with water, dichlorobenzene, low boiling contaminants and acidic compounds to remove overhead the water, dichlorobenzene and low boiling compounds and produce a kettle liquid comprising NMP contaminated with acidic compounds, and
    (b) treating the kettle liquid of said first fractionator by the process of claim 1 to remove acidic compounds; and
    (c) further fractionating the kettle liquid of said first fractionator in a second fractionator to remove overhead a product comprising NMP with treatment of the kettle liquid of said second fractionator by the method of claim 1 to remove acidic compounds with recycle of the treated kettle liquid to said second fractionator.

5. A process for recovery of NMP from poly(phenylene sulfide) production in which fractionation columns are employed in series to remove water, dichlorobenzene and low boiling contaminants from NMP comprising:
    (a) fractionating in a first fractionator NMP contaminated with water, dichlorobenzene, low boiling contaminants and acidic compounds to remove overhead the water, dichlorobenzene and low boiling compounds and produce a kettle liquid comprising NMP contaminated with acidic compounds,
    (b) further fractionating the kettle liquid of said first fractionator in a second fractionator to remove overhead a product comprising NMP, and
    (c) treating said overhead comprising NMP by the process of claim 1 to remove acidic compounds.

6. A process of claim 2 wherein said overhead of (c) comprises acidic compounds and is further treated by contacting said overhead with an amount of an inorganic compound chosen from among the group consisting of alkaline earth carbonates, alkaline earth hydroxides, alkaline earth oxides and alumina sufficient to reduce the acidic compound content of said overhead.

7. A process of claim 3 wherein said overhead of (b) comprises acidic compounds and is further treated by contacting said overhead with an amount of an inorganic compound chosen from among the group consisting of alkaline earth carbonates, alkaline earth hydroxides, alkaline earth oxides and alumina sufficient to reduce the acidic compound content of said overhead.

8. A process of claim 4 wherein said overhead of (c) comprises acidic compounds and is further treated by contacting said overhead with an amount of an inorganic compound chosen from among the group consisting of alkaline earth carbonates, alkaline earth hydroxides, alkaline earth oxides and alumina sufficient to reduce the acidic compound content of said overhead.

9. A method of claim 1 wherein the contacting of NMP with said inorganic compound is conducted by a process of fluidized bed contact of solvent with solid inorganic compound.

10. A method of claim 1 wherein the contacting of NMP with said inorganic compound is conducted by a process of stirred slurry contact of solvent with solid inorganic compound.

11. A process of claim 1 wherein the contacting of NMP with said inorganic compound is conducted by a process of trickle bed contact of solvent with solid inorganic compound.

* * * * *